United States Patent
Kruck et al.

(10) Patent No.: US 11,766,395 B2
(45) Date of Patent: Sep. 26, 2023

(54) PRODUCT FOR DYEING KERATINOUS MATERIAL, CONTAINING AMINOSILICONES AND PIGMENTS IN SPECIFIC WEIGHT RELATIONS

(71) Applicant: Henkel AG & Co. KGaA, Duesseldorf (DE)

(72) Inventors: Constanze Kruck, Grevenbroich (DE); Sandra Hilbig, Bochum (DE); Daniela Kessler-Becker, Leverkusen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/619,896

(22) PCT Filed: Jun. 2, 2020

(86) PCT No.: PCT/EP2020/065216
§ 371 (c)(1),
(2) Date: Dec. 16, 2021

(87) PCT Pub. No.: WO2020/254103
PCT Pub. Date: Dec. 24, 2020

(65) Prior Publication Data
US 2022/0370333 A1    Nov. 24, 2022

(30) Foreign Application Priority Data
Jun. 19, 2019 (DE) .......................... 102019208907.0

(51) Int. Cl.
*A61Q 5/10* (2006.01)
*A61K 8/898* (2006.01)
*A61Q 5/06* (2006.01)

(52) U.S. Cl.
CPC .............. *A61K 8/898* (2013.01); *A61Q 5/065* (2013.01); *A61K 2800/432* (2013.01)

(58) Field of Classification Search
CPC .... A61K 8/898; A61K 2800/432; A61K 8/19; A61K 8/466; A61K 8/492; A61K 8/494; A61K 8/4953; A61K 2800/43; A61Q 5/065
USPC ............................................................ 8/405
See application file for complete search history.

(56) References Cited

U.S. PATENT DOCUMENTS 10,105,308 B2    10/2018  Goutsis et al.
2016/0236655 A1*  8/2016  Natsume ................... B60S 1/08

FOREIGN PATENT DOCUMENTS

| DE | 102013226102 A1 * | 6/2015 | ............. A61Q 5/065 |
| DE | 102014218006 A1 | 3/2016 | |
| EP | 1138317 A2 | 10/2001 | |
| EP | 3058934 A1 | 8/2016 | |
| FR | 3045346 A1 | 6/2017 | |

* cited by examiner

Primary Examiner — Eisa B Elhilo
(74) Attorney, Agent, or Firm — Lorenz & Kopf, LLP

(57) ABSTRACT

It is an object of the present disclosure to provide an agent for coloring keratinous material, in particular human hair, comprising
(a1) at least one amino-functionalized silicone polymer, and
(a2) at least pigment,
the weight ratio of all the pigments (a2) contained in the composition to all the amino-functionalized silicone polymers (a1) contained in the composition, i.e., the weight ratio (a2)/(a1), being not more than 0.95.
A second subject matter is a method for dyeing keratin material, wherein the agent is applied to the keratin material.

19 Claims, No Drawings

PRODUCT FOR DYEING KERATINOUS MATERIAL, CONTAINING AMINOSILICONES AND PIGMENTS IN SPECIFIC WEIGHT RELATIONS

CROSS-REFERENCE TO RELATED APPLICATIONS

This application is a U.S. National-Stage entry under 35 U.S.C. § 371 based on International Application No. PCT/EP2020/065216, filed Jun. 2, 2020, which was published under PCT Article 21(2) and which claims priority to German Application No. 102019208907.0, filed Jun. 19, 2019, which are all hereby incorporated in their entirety by reference.

TECHNICAL FIELD

The subject of the present application is an agent for coloring keratinous material, in particular human hair, which contains at least one amino-functionalized silicone polymer (a1) and at least one pigment (a2), the pigments (a2) and the amino-functionalized silicone polymers (a1) being used in specific weight ratios to one another.

A second object of this application is a method for dyeing keratinous material, in particular human hair, wherein an agent of the first object of the present disclosure is applied to the keratinous material, allowed to act and then washed out again with water.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A challenge that still exists is therefore the search for alternative, high-performance dyes and dyeing processes.

BRIEF SUMMARY

Agents and methods for dyeing keratinous material are provided. In an exemplary embodiment, an agent for dyeing keratinoug material includes an amino-functionalized silicone polymer (a1) and a pigment (a2). A weight ratio of all pigments (a2) in the agent to all the amino-functionalized silicone polymers is not more than 0.95.

A method for dyeing keratinous material is provided in another embodiment. The method includes applying an agent to the keratinous material, where the agent includes an amino-functionalized silicone polymer (a1) and a pigment (a2). A ratio of all the pigments (a2) in the agent to all the amino-functionalized silicone polymers (a1) in the agent is not more than about 0.95. The keratinous material is exposed to the agent, and then the agent is rinsed out of the keratinous material with water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was the object of the present disclosure to provide a dyeing system having color intensities comparable to oxidative dyeing. However, the oxidation dye precursors normally used for this purpose should not be used. A technology was sought that would make it possible to fix the colorant compounds known from the prior art (such as pigments in particular) to the hair in an extremely durable manner. When using the agents in a dyeing process, particularly intensive dyeing results with good fastness properties should be achieved.

Surprisingly, it has now been found that the above-mentioned task can be excellently solved if keratinous materials, in particular hair, are colored with an agent containing at least one amino-functionalized silicone polymer (a1) and at least one pigment (a2) in specific, mutually optimized weight ratios.

A first object of the present disclosure is an agent for coloring keratinous material, in particular human hair, containing determined weight ratios optimized with respect to each other.

(a1) at least one amino-functionalized silicone polymer, and
(a2) at least pigment, the weight ratio of all the pigments (a2) contained in the composition to all the amino-functionalized silicone polymers (a1) contained in the composition, i.e., the weight ratio (a2)/(a1), being not more than about 0.95.

In the course of the work carried out on this disclosure, it was surprisingly found that particularly high color intensities could be achieved in the dyeing of keratin material when the pigments (a2) and the amino silicones (a1) contained in the composition were used in a weight ratio of not more than about 0.95 to each other. In other words, particularly intense colorations could be obtained when the amino silicones (a1) were used in excess by weight compared to the pigments (a2).

Keratinic Material

Keratinous material includes hair, skin, nails (such as fingernails and/or toenails). Wool, furs and feathers also fall under the definition of keratinous material. Preferably, keratinous material is understood to be human hair, human skin and human nails, especially fingernails and toenails. Keratinous material is understood to be human hair.

Coloring Agent

The term "coloring agent" is used in the context of this disclosure for a coloring of the keratin material, in particular the hair, caused using pigments. In this coloring process, the pigments are deposited as coloring compounds in a particularly homogeneous, uniform and smooth film on the surface of the keratin material.

Amino-Functionalized Silicone Polymers (a1)

As the first ingredient (a1) essential to the present disclosure, the composition contains at least one amino-functionalized silicone polymer. The amino-functionalized silicone polymer may alternatively be referred to as amino silicone or amodimethicone.

Silicone polymers are generally macromolecules with a molecular weight of at least about 500 g/mol, preferably at least about 1000 g/mol, more preferably at least about 2500 g/mol, particularly preferably at least about 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than about $10^7$ g/mol, preferably not more than about $10^6$ g/mol, and particularly preferably not more than about $10^5$ g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than about 10 Si—O repeat units, preferably more than about 50 Si—O repeat units, and more preferably more than about 100 Si—O repeat units, most preferably more than about 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, good effects could be obtained with amino-functionalized silicone polymers (a1) if they carry at least one primary, at least one secondary and/or at least one tertiary amino group. However, colorations with the highest color intensities were observed when an amino-functionalized silicone polymer (a1) containing at least one secondary amino group was used in the agent.

In a very particularly preferred embodiment, an agent according to the present disclosure is exemplified in that the composition comprises at least one amino-functionalized silicone polymer (a1) having at least one secondary amino group.

The secondary amino group(s) may be located at various positions on the amino-functionalized silicone polymer.

Particularly good effects were found when an amino-functionalized silicone polymer (a1) was used that has at least one, preferably several, structural units of the formula (Si amino).

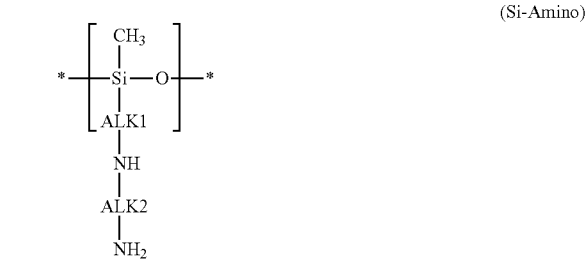

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, an agent according to the present disclosure is exemplified in that the agent contains at least one amino-functionalized silicone polymer (a1) comprising at least one structural unit of the formula (Si amino),

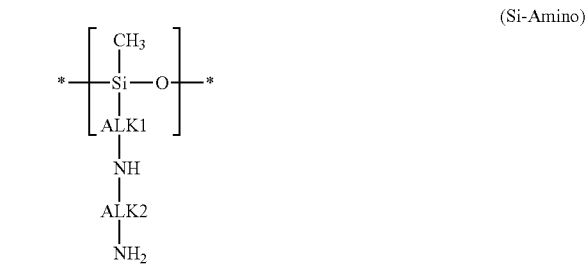

(Si-Amino)

where

ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A divalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In another particularly preferred embodiment, the structural units of the formula (Si amino) represent repeat units in the amino-functionalized silicone polymer (a1), so that the silicone polymer comprises multiple structural units of the formula (Si amino).

Particularly well-suited amino-functionalized silicone polymers (a1) with at least one secondary amino group are listed below.

Colorations with the very highest color intensities could be obtained when an agent containing at least one amino-functionalized silicone polymer (a1) comprising structural units of the formula (Si-I) and of the formula (Si-II) was applied to the keratinous material

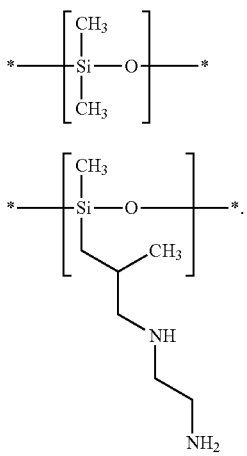

In a further explicitly quite particularly preferred embodiment, an agent according to the present disclosure is exemplified in that it contains at least one amino-functionalized silicone polymer (a1) comprising structural units of the formula (Si-I) and of the formula (Si-II)

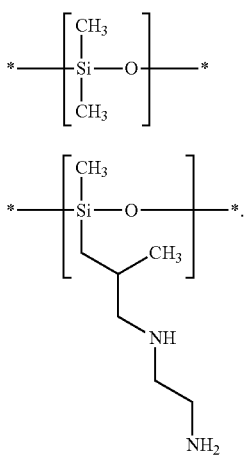

A corresponding amino functionalized silicone polymer with the structural units (Si-I) and (Si-II) is, for example, the commercial product DC 2-8566 or Dowsil® 2-8566 Amino Fluid, which is commercially distributed by the Dow® Chemical Company and bears the designation "Siloxanes and Silicones, 3-[(2-aminoethyl)amino]-2-methylpropyl Me, Di-Me-Siloxane" and the CAS number 106842-44-8.

In another preferred embodiment, an agent according to the present disclosure is exemplified in that it comprises at least one amino-functional silicone polymer (a1) of the formula of the formula (Si-III),

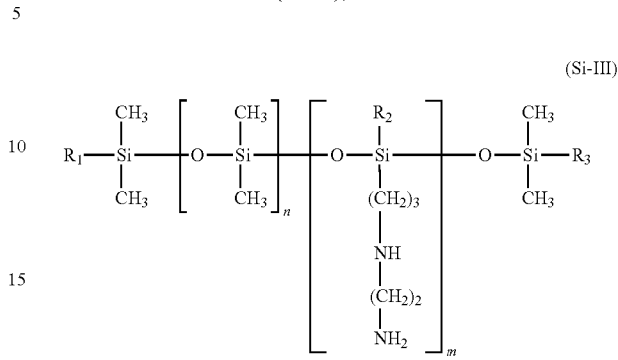

where
a. m and n mean numbers chosen so that the sum (n+m) is in the range 1 to about 1000,
b. n is a number in the range 0 to about 999 and m is a number in the range 1 to about 1000,
c. R1, R2 and R3, which are the same or different, denote a hydroxy group or a C1-4 alkoxy group,
d. wherein at least one of R1 to R3 represents a hydroxy group;

Other compositions preferred according to the present disclosure are exemplified by their content of at least one amino-functional silicone polymer (a1) of the formula of the formula (Si-IV),

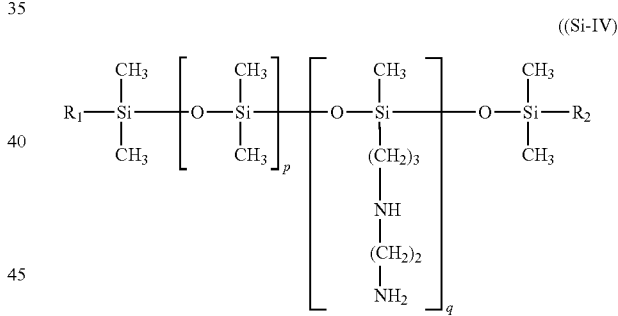

located in the
a. p and q mean numbers chosen so that the sum (p+q) is in the range 1 to about 1000,
b. p is a number in the range 0 to about 999 and q is a number in the range 1 to about 1000,
c. R1 and R2, which are different, denote a hydroxy group or a $C_1$-4 alkoxy group, at least one of R1 to R2 denoting a hydroxy group.

The silicones of the formulas (Si-III) and (Si-IV) differ in the grouping at the Si atom, which carries the nitrogen-containing group: In formula (Si-III), R2 represents a hydroxy group or a C1-4 alkoxy group, while the residue in formula (Si-IV) is a methyl group. The individual Si groupings, which are marked with the indices m and n or p and q, do not have to be present as blocks; rather, the individual units can also be present in a statistically distributed manner, i.e., in the formulas (Si-III) and (Si-IV), not every R1-Si $(CH_3)_2$ group is necessarily bonded to an —[O—$Si(CH_3)_2$] grouping.

Agents according to the present disclosure which contain at least one amino-functional silicone polymer (a1) of the formula of the formula (Si-V) have also proved to be particularly effective with respect to the desired effects

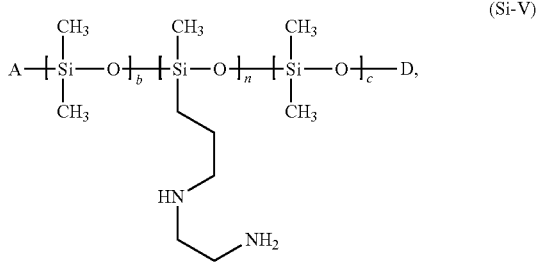
(Si-V)

located in the
A represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
b, n and c stand for integers between 0 and about 1000, with the specifications
n>0 and b+c>0
at least one of the conditions A=—OH or D=—H is fulfilled.

In the above formula (Si-V), the individual siloxane units are statistically distributed with the indices b, c and n, i.e., they do not necessarily have to be block copolymers.

Agent (a) may further comprise one or more different amino-functionalized silicone polymers represented by the formula (Si-VI)

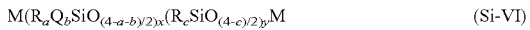
(Si-VI)

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2,000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably R is an alkyl radical containing from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional residue containing at least one amino functional group. One possible formula for Z is NH(CH$_2$)$_z$NH$_2$, where z is 1 or more. Another possible formula for Z is —NH(CH$_2$)$_z$(CH 2)$_{zz}$NH, wherein both z and zz are independently 1 or more, this structure comprising diamino ring structures, such as piperazinyl. Z is most preferably an —NHCH$_2$CH 2NH$_2$ residue. Another possible formula for Z is —N(CH$_2$)$_z$(CH$_2$)$_{zz}$NX$_2$ or —NX$_2$, wherein each X of X$_2$ is independently selected from the group of hydrogen and alkyl groups having 1 to about 12 carbon atoms, and zz is 0.

Q is most preferably a polar, amine-functional radical of the formula —CH$_2$CH$_2$CH$_2$NHCH$_2$CH$_2$NH$_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$ SiO$_{(4-a-b)/2}$ units to R$_c$SiO$_{(4-c)/2}$ units is in the range of about 1:2 to about 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In another preferred embodiment, an agent according to the present disclosure is exemplified in that it comprises at least one amino-functional silicone polymer of the formula (Si-VII),

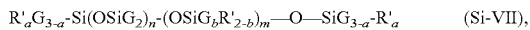
(Si-VII), wherein:
G is —H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;
a stands for a number between 0 and 3, especially 0;
b stands for a number between 0 and 1, especially 1,
m and n are numbers whose sum (m+n) is between 1 and about 2000, preferably between about 50 and about 150, where n preferably assumes values from 0 to about 1999 and from about 49 to about 149 and m preferably assumes values from 1 to about 2000, in particular from 1 to 10,
R' is a monovalent radical selected from
-Q-N(R")—CH$_2$—CH$_2$—N(R")$_2$
-Q-N(R")$_2$
-Q-N$^+$(R")$_3$A$^-$
-Q-N$^+$H(R")$_2$A$^-$
-Q-N$^+$H$_2$(R")A$^-$
-Q-N(R")—CH$_2$—CH$_2$—N$^+$R"H$_2$A$^-$,
where each Q is a chemical bond, —CH$_2$—, —CH$_2$CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—,
R" represents identical or different radicals selected from the group of —H, -phenyl, -benzyl, —CH$_2$—CH(CH$_3$) Ph, the C$_{1-20}$ alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion preferably selected from chloride, bromide, iodide or methosulfate.

In the context of a further preferred embodiment, an agent according to the present disclosure is exemplified in that it comprises at least one amino-functional silicone polymer (a1) of the formula (Si-VIIa),

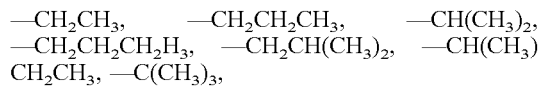

(Si-VIIa)

wherein m and n are numbers whose sum (m+n) is between 1 and about 2000, preferably between about 50 and about 150, n preferably assuming values from 0 to about 1999 and from about 49 to about 149, and m preferably assuming values from 1 to about 2000, in particular from 1 to 10.

According to the INCI declaration, these silicones are called trimethylsilylamodimethicones.

In the context of a further preferred embodiment, an agent according to the present disclosure is exemplified in that it comprises at least one amino-functional silicone polymer of the formula (Si-VIIb)

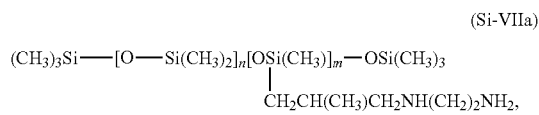

(Si-VIIb)

in which R represents —OH, —O—CH$_3$ or a —CH$_3$ group and m, n1 and n2 are numbers whose sum (m+n1+n2) is between 1 and about 2000, preferably between about 50 and about 150, the sum (n1+n2) preferably assuming values from 0 to about 1999 and from about 49 to about 149 and m preferably assuming values from 1 to 2000, in particular from 1 to 10.

According to the INCI declaration, these amino-functionalized silicone polymers are called amodimethicones.

Regardless of which amino-functional silicones are used, agents according to the present disclosure are preferred which contain an amino-functional silicone polymer (a1) whose amine number is above about 0.25 meq/g, preferably above about 0.3 meq/g and above about 0.4 meq/g. The amine number represents the milliequivalents of amine per gram of the amino-functional silicone. The amine number represents the milliequivalents of amine per gram of the amino-functional silicone.

Furthermore, agents containing a special 4-morpholinomethyl-substituted silicone polymer (a1) are also suitable. This amino-functionalized silicone polymer comprises structural units of the formulae (SI-VIII) and of the formula (Si-IX)

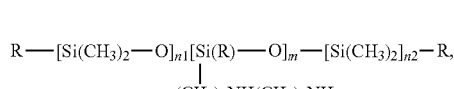

(Si-VIII)

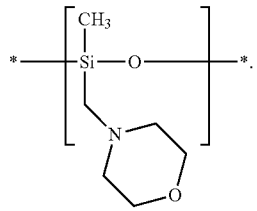

(Si-IX)

Corresponding 4-morpholinomethyl-substituted silicone polymers are described below.

A preferred amino-functionalized silicone polymer is known as: Amodimethicone/Morpholinomethyl Silsesquioxane Copolymer is known and commercially available from Wacker® in the form of the raw material Belsil® ADM 8301 E.

As a 4-morpholinomethyl-substituted silicone, for example, a silicone can be used which has structural units of the formulae (Si-VIII), (Si-IX) and (Si-X)

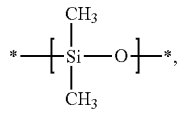

(Si-VIII)

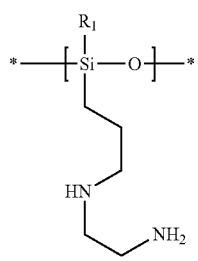

(Si-X)

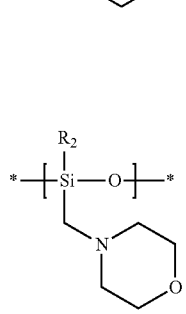

(Si-IX)

in which
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.

Particularly preferred compositions according to the present disclosure contain at least one 4-morpholinomethyl-substituted silicone of the formula (Si-XI)

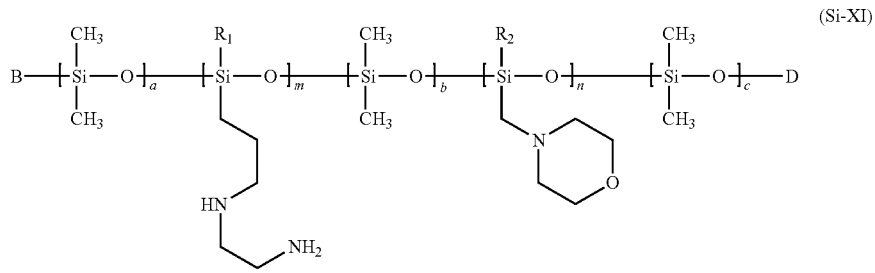

(Si-XI)

wherein
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.
B represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$, a, b and c stand independently for integers between 0 and about 1000, with the condition a+b+c>0
m and n independently of each other stand for integers between 1 and about 1000
with the proviso that
at least one of the conditions B=—OH or D=—H is fulfilled,
the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m and n are preferably statistically distributed.

The silicones used according to the present disclosure represented by formula (Si-VI) can be trimethylsilyl-terminated (D or B=—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which:

| | |
|---|---|
| B = —O—Si(CH$_3$)$_2$OH and | D = —Si(CH$_3$)$_3$ |
| B = —O—Si(CH$_3$)$_2$OH and | D = —Si(CH$_3$)$_2$OH |
| B = —O—Si(CH$_3$)$_2$OH and | D = —Si(CH$_3$)$_2$OCH$_3$ |
| B = —O—Si(CH$_3$)$_3$ and | D = —Si(CH$_3$)$_2$OH |
| B = —O—Si(CH$_3$)$_2$OCH$_3$ and | D = —Si(CH$_3$)$_2$OH |

These silicones lead to exorbitant improvements in the hair properties of the hair treated with the agents of the present disclosure, and to a seriously improved protection in oxidative treatment.

It has been found to be particularly advantageous if the agent according to the present disclosure contains the amino-functionalized silicone polymer(s) (a1) in certain quantity ranges. Particularly good results were obtained when the agent contained—based on the total weight of the agent—a total amount of about 0.1 to about 8.0% by weight, preferably about 0.2 to about 5.0% by weight, more preferably about 0.3 to about 3.0% by weight, and most preferably about 0.4 to about 2.5% by weight.

In another particularly preferred embodiment, an agent according to the present disclosure is exemplified in that it contains—based on the total weight of the agent—one or more amino-functionalized silicone polymers (a1) in a total amount of from about 0.1 to about 8.0% by weight, preferably from about 0.2 to about 5.0% by weight, more preferably from about 0.3 to about 3.0% by weight and very particularly preferably from about 0.4 to about 2.5% by weight.

Pigments (a2)

As a second essential component, the composition according to the present disclosure contains at least one pigment (a2).

For the purposes of the present disclosure, colorant compounds are substances capable of imparting a coloration to the keratin material. Particularly well-suited colorant compounds can be selected from the group of pigments, direct-acting dyes, photochromic dyes and thermochromic dyes.

An agent according to the present disclosure is exemplified in that it contains at least one colorant compound (a2) from the group of pigments.

Pigments within the meaning of the present disclosure are coloring compounds which have a solubility in water at 25° C. of less than about 0.5 g/L, preferably less than about 0.1 g/L, even more preferably less than about 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent according to the present disclosure is exemplified in that it comprises at least one colorant compound (a2) from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

According to the present disclosure, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent according to the present disclosure is exemplified in that it comprises at least one inorganic pigment (a2) which is preferably selected from the group of colored metal oxides, metal hydroxides, metal oxide hydrates, silicates, metal sulfides, complex metal cyanides, metal sulfates, bronze pigments and/or colored mica- or mica-based pigments coated with at least one metal oxide and/or a metal oxychloride.

In a further preferred embodiment, a composition according to the present disclosure is exemplified in that it comprises at least one colorant compound (a2) from the group of pigments selected from mica- or mica-based pigments which are reacted with one or more metal oxides from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck®, Ariabel® and Unipure® from Sensient, Prestige® from Eckart® Cosmetic Colors and Sunshine® from Sunstar®.

Particularly preferred color pigments with the trade name Colorona® are, for example:
Colorona® Copper, Merck®, MICA, CI 77491 (IRON OXIDES)
Colorona® Passion Orange, Merck®, Mica, CI 77491 (Iron Oxides), Alumina
Colorona® Patina Silver, Merck®, MICA, CI 77499 (IRON OXIDES), CI 77891 (TITANIUM DIOXIDE)
Colorona® RY, Merck®, CI 77891 (TITANIUM DIOXIDE), MICA, CI 75470 (CARMINE)
Colorona® Oriental Beige, Merck®, MICA, CI 77891 (TITANIUM DIOXIDE), CI 77491 (IRON OXIDES)
Colorona® Dark Blue, Merck®, MICA, TITANIUM DIOXIDE, FERRIC FERROCYANIDE
Colorona® Chameleon, Merck®, CI 77491 (IRON OXIDES), MICA
Colorona® Aborigine Amber, Merck®, MICA, CI 77499 (IRON OXIDES), CI 77891 (TITANIUM DIOXIDE)
Colorona® Blackstar Blue, Merck®, CI 77499 (IRON OXIDES), MICA
Colorona® Patagonian Purple, Merck®, MICA, CI 77491 (IRON OXIDES), CI 77891 (TITANIUM DIOXIDE), CI 77510 (FERRIC FERROCYANIDE)
Colorona® Red Brown, Merck®, MICA, CI 77491 (IRON OXIDES), CI 77891 (TITANIUM DIOXIDE)
Colorona® Russet, Merck®, CI 77491 (TITANIUM DIOXIDE), MICA, CI 77891 (IRON OXIDES)
Colorona® Imperial Red, Merck®, MICA, TITANIUM DIOXIDE (CI 77891), D&C RED NO. 30 (CI 73360)
Colorona® Majestic Green, Merck®, CI 77891 (TITANIUM DIOXIDE), MICA, CI 77288 (CHROMIUM OXIDE GREENS)
Colorona® Light Blue, Merck®, MICA, TITANIUM DIOXIDE (CI 77891), FERRIC FERROCYANIDE (CI 77510)
Colorona® Red Gold, Merck®, MICA, CI 77891 (TITANIUM DIOXIDE), CI 77491 (IRON OXIDES)
Colorona® Gold Plus MP 25, Merck®, MICA, TITANIUM DIOXIDE (CI 77891), IRON OXIDES (CI 77491)
Colorona® Carmine Red, Merck®, MICA, TITANIUM DIOXIDE, CARMINE
Colorona® Blackstar Green, Merck®, MICA, CI 77499 (IRON OXIDES)
Colorona® Bordeaux, Merck®, MICA, CI 77491 (IRON OXIDES)
Colorona® Bronze, Merck®, MICA, CI 77491 (IRON OXIDES)
Colorona® Bronze Fine, Merck®, MICA, CI 77491 (IRON OXIDES)
Colorona® Fine Gold MP 20, Merck®, MICA, CI 77891 (TITANIUM DIOXIDE), CI 77491 (IRON OXIDES)
Colorona® Sienna Fine, Merck®, CI 77491 (IRON OXIDES), MICA
Colorona® Sienna, Merck®, MICA, CI 77491 (IRON OXIDES)
Colorona® Precious Gold, Merck®, Mica, CI 77891 (Titanium dioxide), Silica, CI 77491 (Iron oxides), Tin oxide
Colorona® Sun Gold Sparkle MP 29, Merck®, MICA, TITANIUM DIOXIDE, IRON OXIDES, MICA, CI 77891, CI 77491 (EU)
Colorona® Mica Black, Merck®, CI 77499 (Iron oxides), Mica, CI 77891 (Titanium dioxide)
Colorona® Bright Gold, Merck®, Mica, CI 77891 (Titanium dioxide), CI 77491 (Iron oxides)
Colorona® Blackstar Gold, Merck®, MICA, CI 77499 (IRON OXIDES)

Other particularly preferred color pigments with the trade name Xirona® are for example:
Xirona® Golden Sky, Merck®, Silica, CI 77891 (Titanium Dioxide), Tin Oxide
Xirona® Caribbean Blue, Merck®, Mica, CI 77891 (Titanium Dioxide), Silica, Tin Oxide
Xirona® Kiwi Rose, Merck®, Silica, CI 77891 (Titanium Dioxide), Tin Oxide
Xirona® Magic Mauve, Merck®, Silica, CI 77891 (Titanium Dioxide), Tin Oxide.

In addition, particularly preferred color pigments with the trade name Unipure® are for example:
Unipure® Red LC 381 EM, Sensient CI 77491 (Iron Oxides), Silica
Unipure® Black LC 989 EM, Sensient, CI 77499 (Iron Oxides), Silica
Unipure® Yellow LC 182 EM, Sensient, CI 77492 (Iron Oxides), Silica In a further embodiment, the composition according to the present disclosure may also comprise one or more colorant compounds (a2) selected from the group of organic pigments The organic pigments according to the present disclosure are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyorrole, indigo, thioindido, dioxazine and/or triarylmethane compounds.

Examples of particularly suitable organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred embodiment, a composition according to the present disclosure is exemplified in that it comprises at least one organic pigment (a2) which is preferably selected from the group of carmine, quinacridone, phthalocyanine, sorghum, blue pigments having the color index numbers Cl 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. In the sense of the present disclosure, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above-mentioned pigments in the agent according to the present disclosure is particularly preferred. It is also preferred if the pigments used have a certain particle size. According to the present disclosure, it is therefore advantageous if the at least one pigment has an average particle size $D_{50}$ of about 1.0 to about 50 μm, preferably about 5.0 to about 45 μm, preferably about 10 to about 40 μm, about 14 to about 30 μm. The mean particle size $D_{50}$, for example, can be determined using dynamic light scattering (DLS).

The pigments (a2) represent the second essential of the agent according to the present disclosure and are preferably used in the agent in certain ranges of amounts.

Particularly good results were obtained when the agent contained—based on the total weight of the agent—one or more pigments (a2) in a total amount of about 0.01 to about 10.0% by weight, preferably about 0.1 to about 5.0% by weight, further preferably about 0.2 to about 2.5% by weight and very preferably about 0.25 to about 1.5% by weight.

In another very particularly preferred embodiment, an agent according to the present disclosure is exemplified in that the agent contains—based on the total weight of the agent—one or more pigments (a2) in a total amount of from about 0.01 to about 10.0% by weight, preferably from about 0.1 to about 5.0% by weight, more preferably from about 0.2 to about 2.5% by weight and very particularly preferably from about 0.25 to about 1.5% by weight.

In another very particularly preferred embodiment, an agent according to the present disclosure is exemplified in that the agent contains—based on the total weight of the agent—one or more inorganic pigments (a2) in a total amount of from about 0.01 to about 10.0% by weight, preferably from about 0.1 to about 5.0% by weight, more preferably from about 0.2 to about 2.5% by weight and very particularly preferably from about 0.25 to about 1.5% by weight.

In another very particularly preferred embodiment, an agent according to the present disclosure is exemplified in that the agent contains—based on the total weight of the agent—one or more organic pigments (a2) in a total amount of from about 0.01 to about 10.0% by weight, preferably from about 0.1 to about 5.0% by weight, more preferably from about 0.2 to about 2.5% by weight and very particularly preferably from about 0.25 to about 1.5% by weight.

Weight Ratio (a2)/(a1)

A further feature of the composition according to the present disclosure is the weight ratio of all pigments (a2) contained in the composition to all amino-functionalized silicone polymers (a1) contained in the composition, i.e., the weight ratio (a2)/(a1), which may be at a value of not more than about 0.95.

In other words, the weight ratio (a2)/(a1) is such that the total amount of all the amino silicones (a1) contained in the composition is increased by a factor of at least about 1.05 compared with all the pigments contained in the composition. Thus, compared with the pigments (a2), the amino silicones (a1) are used in excess by weight.

In the experiments leading to the present disclosure, it was observed that application of the agent of the present disclosure to the keratin material resulted in the formation of a film, with the amino silicone(s) (a1) enclosing the keratin material and the pigments (a2) being embedded or incorporated in this film. The series tests carried out in this connection showed that with an increase in the amount of amino silicone (a1) used, it was possible to achieve an intensification of the color result, even if the total amount of pigments (a2) remained the same on average.

Here, the color intensity was already significantly improved at a weight ratio (a2)/(a1) of maximum about 0.95. However, even better results were obtained when the weight ratio (a2)/(a1) was adjusted to a value in the range from about 0.10 to about 0.80, preferably from about 0.20 to about 0.70, more preferably from about 0.25 to about 0.65, still more preferably from about 0.30 to about 0.60, still more preferably from about 0.35 to about 0.55, and most preferably from about 0.35 to about 0.45.

In the context of a further embodiment, an explicitly quite particularly preferred agent is exemplified in that the weight ratio of all pigments (a2) contained in the agent to all amino-functionalized silicone polymers (a1) contained in the agent, i.e. the weight ratio (a2)/(a1), is from about 0.10 to about 0.80, preferably from about 0.20 to about 0.70, more preferably from about 0.25 to about 0.65, still more preferably from about 0.30 to about 0.60, still more preferably from about 0.35 to about 0.55 and very particularly preferably from about 0.35 to about 0.45.

Example: 100 g of agent according to the present disclosure contain
0.2 g pigment CI 42090 and
0.2 g pigment CI 69800 and
0.2 g pigment CI 69825 and
0.2 g pigment CI 73000 and
0.2 g pigment CI 74100 and
1.5 g amino silicone (ex. Dowsil® 2-8566 Amino Fluid)
Total amount of pigments (a2)=1.0 g
Total amount of amino-functionalized silicone polymers (a1)=1.5 g
Weight ratio (a2)/(a1)=0.66

Example: 100 g of agent according to the present disclosure contain
0.5 g pigment Cl 42090 and
0.5 g pigment CI 69825 and
2.5 g amino silicone (ex. Dowsil® 2-8566 Amino Fluid)
Total amount of pigments (a2)=1.0 g
Total amount of amino-functionalized silicone polymers (a1)=2.5 g
Weight ratio (a2)/(a1)=0.40

Fat Components on Average

It has been found that the use of at least one fatty component in the composition according to the present disclosure results in the composition being in the form of an emulsion, which has the optimum viscosity and has also been found to be advantageous in terms of improving color intensity. For this reason, the composition according to the present disclosure may further comprise a fat component as a further optional ingredient.

The fatty components are hydrophobic substances that can form emulsions in the presence of water, forming micelle systems. Without being committed to this theory, it is assumed that the $C_1$-$C_6$ alkoxysilanes—either in the form of their monomers or possibly in the form of their condensed oligomers—are embedded in this hydrophobic environment or in the micelle systems so that the polarity of their environment changes. Due to the hydrophobic nature of the fatty components, the environment of the $C_1$-$C_6$ alkoxysilanes is also hydrophobized. It is assumed that the polymerization reaction of the $C_1$-$C_6$ alkoxy silanes leading to the film or coating takes place in an environment of reduced polarity at reduced speed.

For the purposes of the present disclosure, "fatty components" means organic compounds with a solubility in water at room temperature (22° C.) and atmospheric pressure (760 mmHg) of less than about 1% by weight, preferably less than about 0.1% by weight. The definition of fat constituents explicitly covers only uncharged (i.e., non-ionic) compounds. Fat components have at least one saturated or unsaturated alkyl group with at least about 12 C atoms. The molecular weight of the fat constituents is a maximum of about 5000 g/mol, preferably a maximum of about 2500 g/mol and particularly preferably a maximum of about 1000 g/mol. The fat components are neither polyoxyalkylated nor polyglycerylated compounds.

Very preferably, the additional fatty components used in the composition can be selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In the context of a further preferred embodiment, an agent according to the present disclosure is exemplified in that it contains one or more fat constituents from the group of the $C_{12}$-$C_{30}$ fatty alcohols, the $C_{12}$-$C_{30}$ fatty acid triglycerides, the $C_{12}$-$C_{30}$ fatty acid monoglycerides, the $C_{12}$-$C_{30}$ fatty acid diglycerides and/or the hydrocarbons.

In this context, very particularly preferred fat constituents are understood to be constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. For the purposes of the present disclosure, only non-ionic substances are explicitly regarded as fat components. Charged compounds such as fatty acids and their salts are not considered to be fat components.

The $C_{12}$-$C_{30}$ fatty alcohols can be saturated, mono- or polyunsaturated, linear or branched fatty alcohols with about 12 to about 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

In a further preferred embodiment, an agent according to the present disclosure is exemplified in that it comprises one or more $C_{12}$-$C_{30}$ fatty alcohols (a4) selected from the group of
Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol),
Arachyl alcohol (eicosan-1-ol),
Heneicosyl alcohol (heneicosan-1-ol),
Behenyl alcohol (docosan-1-ol),
(9Z)-Octadec-9-en-1-ol (oleyl alcohol),
(9E)-Octadec-9-en-1-ol (elaidyl alcohol),
(9Z,12Z)-Octadeca-9,12-dien-1-ol (linoleyl alcohol),
(9Z,12Z,15Z)-Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol contains.

It has been found to be quite preferable to use one or more $C_{12}$-$C_{30}$ fatty alcohols in quite specific ranges of amounts.

Furthermore, it is particularly preferred if the composition contains one or more $C_{12}$-$C_{30}$ fatty alcohols in a total amount of from about 2.0 to about 50.0% by weight, preferably from about 3.0 to about 30.0% by weight, more preferably from about 4.0 to about 20.0% by weight, still more preferably from about 5.0 to about 15.0% by weight and most preferably from about 5.0 to about 10.0% by weight, based on the total weight of the composition.

Further, as a wholly suitable fat ingredient, the composition may also contain at least one $C_{12}$-$C_{30}$ fatty acid triglyceride that is $C_{12}$-$C_{30}$ fatty acid monoglyceride and/or $C_{12}$-$C_{30}$ fatty acid diglyceride. For the purposes of the present disclosure, a $C_{12}$-$C_{30}$ fatty acid triglyceride is understood to be the triester of the trivalent alcohol glycerol with three equivalents of fatty acid. Both structurally identical and different fatty acids within a triglyceride molecule can be involved in the formation of esters.

According to the present disclosure, fatty acids are to be understood as saturated or unsaturated, unbranched or branched, unsubstituted or substituted $C_{12}$-$C_{30}$ carboxylic acids. Unsaturated fatty acids can be mono- or polyunsaturated. For an unsaturated fatty acid, its C—C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product according to the present disclosure.

A $C_{12}$-$C_{30}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when the composition contained at least one $C_{12}$-$C_{30}$ fatty acid monoglyceride selected from the monoesters of glycerol with one equivalent of fatty acid selected from the group of dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselic acid [(Z)-6-octadecenoic acid], Palmitoleic acid [(9Z)-Hexadec-9-enoic acid], Oleic acid [(9Z)-Octadec-9-enoic acid], Elaidic acid [(9E)-Octadec-9-enoic acid], Erucic acid [(13Z)-Docos-13-enoic acid], Linoleic acid [(9Z,12Z)-Octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

In the context of a further embodiment, a composition according to the present disclosure is exemplified in that it comprises at least one $C_{12}$-$C_{30}$ fatty acid monoglyceride selected from the monoesters of glycerol with one equivalent of fatty acid from the group of dodecanoic acid, tetradecanoic acid, hexadecanoic acid, tetracosanoic acid, octadecanoic acid, eicosanoic acid and/or docosanoic acid.

It has been shown to be preferable to use one or more $C_{12}$-$C_{30}$ fatty acid mono-, $C_{12}$-$C_{30}$ fatty acid di- and/or $C_{12}$-$C_{30}$ fatty acid triglycerides (a4) in very specific ranges of amounts in the composition.

Regarding the solution of the problem according to the present disclosure, it has proved advantageous if the composition—based on the total weight of the composition—contained one or more $C_{12}$-$C_{30}$ fatty acid mono-, $C_{12}$-$C_{30}$ fatty acid di- and/or $C_{12}$-$C_{30}$ fatty acid triglycerides (a4) in a total amount of about 0.1 to about 20.0 wt.-%, preferably from about 0.3 to about 15.0% by weight, more preferably from about 0.5 to about 10.0% by weight and most preferably from about 0.8 to about 5.0% by weight.

In a very particularly preferred embodiment, a process according to the present disclosure is exemplified in that the composition contains—based on the total weight of the composition—one or more $C_{12}$-$C_{30}$ fatty acid mono-, $C_{12}$-$C_{30}$ fatty acid di- and/or $C_{12}$-$C_{30}$ fatty acid triglycerides in a total amount of from about 0.1 to about 20.0% by weight, preferably from about 0.3 to about 15.0% by weight, more preferably from about 0.5 to about 10.0% by weight and very particularly preferably from about 0.8 to about 5.0% by weight.

The $C_{12}$-$C_{30}$ fatty acid mono-, $C_{12}$-$C_{30}$ fatty acid di- and/or $C_{12}$-$C_{30}$ fatty acid triglycerides may be used as the sole fat components (a4) in the compositions. However, it may also be suitable according to the present disclosure to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into the composition.

Furthermore, as a very particularly preferred fat constituent, the composition may also contain at least one hydrocarbon.

Hydrocarbons are compounds composed exclusively of the atoms carbon and hydrogen with 8 to about 80 C atoms. In this context, aliphatic hydrocarbons such as mineral oils, liquid paraffin oils (e.g., Paraffinium Liquidum or Paraffinum Perliquidum), isoparaffin oils, semi-solid paraffin oils, paraffin waxes, hard paraffin (Paraffinum Solidum), vaseline and polydecenes are particularly preferred.

Liquid paraffin oils (Paraffinum Liquidum and Paraffinium Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, composed mainly of hydrocarbon chains with a C-chain distribution of about 25 to about 35 C-atoms.

Particularly good results were obtained when the composition contained at least one hydrocarbon selected from the group of mineral oils, liquid kerosene oils, isoparaffin oils, semisolid kerosene oils, kerosene waxes, hard kerosene (paraffinum solidum), petrolatum and polydecenes.

In a very particularly preferred embodiment, an agent according to the present disclosure is exemplified in that it contains at least one fatty constituent from the group of hydrocarbons.

Regarding the solution of the problem according to the present disclosure, it proved to be quite particularly preferable if the composition contained—based on the total weight of the composition—one or more hydrocarbons in a total amount of from about 0.5 to about 20.0% by weight, preferably from about 0.7 to about 10.0% by weight, more preferably from about 0.9 to about 5.0% by weight and very particularly preferably from about 1.0 to about 4.0% by weight.

In a very particularly preferred embodiment, an agent according to the present disclosure is exemplified in that it contains—based on the total weight of the agent—one or more hydrocarbons in a total amount of in a total amount of from about 0.5 to about 20.0% by weight, preferably from about 0.7 to about 10.0% by weight, more preferably from about 0.9 to about 5.0% by weight and very particularly preferably from about 1.0 to about 4.0% by weight.

The hydrocarbon or hydrocarbons may be used as the sole fatty ingredients in the agents. However, it is also according to the present disclosure to incorporate at least one hydrocarbon in combination with at least one other constituent into the compositions.

Very preferably, the composition contains at least one fatty constituent from the group of $C_{12}$-$C_{30}$ fatty alcohols and at least one further fatty constituent from the group of hydrocarbons.

Average Water Content

The agent described above is a ready-to-use agent that can be applied to the keratinous material. This ready-to-use agent preferably has a high water content. It has been found that particularly suitable agents are those containing—based on the total weight of the agent—about 50.0 to about 98.0% by weight, preferably about 60.0 to about 90.0% by weight, more preferably about 70.0 to about 90.0% by weight and most preferably about 75.0 to about 90.0% by weight of water.

In a further explicitly quite particularly preferred embodiment, an agent according to the present disclosure is exemplified in that it contains—based on the total weight of the agent—about 50.0 to about 98.0% by weight, preferably about 60.0 to about 90.0% by weight, further preferably about 70.0 to about 90.0% by weight and very particularly preferably about 75.0 to about 90.0% by weight of water.

Surfactants in the Medium

Due to the optional but preferred content of water and fat constituent, the agent according to the present disclosure is particularly preferably in the form of an emulsion. To further optimize the formation of the emulsion, it has proven particularly preferable to continue to use at least one surfactant in the agent.

Very preferably, therefore, the composition additionally contains at least one surfactant.

In the context of a further particularly preferred embodiment, an agent according to the present disclosure is exemplified in that it comprises at least one surfactant.

The term surfactants (T) refer to surface-active substances that can form adsorption layers on surfaces and interfaces or aggregate in bulk phases to form micelle colloids or lyotropic mesophases. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

In a very particularly preferred embodiment, an agent according to the present disclosure is exemplified in that it comprises at least one nonionic surfactant.

Non-ionic surfactants contain, for example, a polyol group, a polyalkylene glycol ether group or a combination of polyol and polyglycol ether group as the hydrophilic group. Such links include Addition products of about 2 to about 50 mol ethylene oxide and/or 0 to about 5 mol propylene oxide to linear and branched fatty alcohols with 6 to about 30 C atoms, the fatty alcohol polyglycol ethers or the fatty alcohol polypropylene glycol ethers or mixed fatty alcohol polyethers, Addition products of about 2 to about 50 mol ethylene oxide and/or 0 to about 5 mol propylene oxide to linear and branched fatty acids with 6 to about 30 C atoms, the fatty acid polyglycol ethers or the fatty acid polypropylene glycol ethers or mixed fatty acid polyethers, Addition products of about 2 to about 50 mol ethylene oxide and/or 0 to about 5 mol propylene oxide to linear and branched alkylphenols having 8 to about 15 C atoms in the alkyl group, the alkylphenol polyglycol ethers or the alkylpolypropylene glycol ethers or mixed alkylphenol polyethers, with a methyl or $C_2$-$C_6$-alkyl radical end-group capped addition products of about 2 to about 50 moles of ethylene oxide and/or 0 to about 5 moles of propylene oxide to linear and branched fatty alcohols with 8 to about 30 C atoms, to fatty acids with 8 to about 30 C atoms and to alkylphenols with 8 to about 15 C atoms in the alkyl group, such as the grades available under the sales names Dehydol® LS, Dehydol® LT (Cognis), $C_{12}$-$C_{30}$ fatty acid mono- and diesters of addition products of about 1 to about 30 mol ethylene oxide to glycerol, Addition products of about 5 to about 60 mol ethylene oxide to castor oil and hardened castor oil, Polyol fatty acid esters, such as the commercial product Hydagen® HSP (Cognis) or Sovermol® grades (Cognis), alkoxylated triglycerides, alkoxylated fatty acid alkyl esters of the formula (Tnio-1)

$$R^1CO-(OCH_2CHR^2)_w OR^3 \quad \text{(Tnio-1)}$$

in which $R^1CO$ is a linear or branched, saturated and/or unsaturated acyl radical having 6 to about 22 carbon atoms, $R^2$ is hydrogen or methyl, $R^3$ is linear or branched alkyl radicals having 1 to 4 carbon atoms and w is numbers from 1 to about 20, amine oxides, Hydroxy mixed ethers, as described for example in DE-OS 19738866, Sorbitan fatty acid esters and addition products of ethylene oxide to sorbitan fatty acid esters such as polysorbates, Sugar fatty acid esters and addition products of ethylene oxide to sugar fatty acid ester, Addition products of ethylene oxide to fatty acid alkanolamides and fatty amines, Sugar tensides of the alkyl and alkenyl oligoglycoside type according to formula (E4-II), $$R^4O-[G]_p \quad \text{(Tnio-2)}$$

in which $R^4$ is an alkyl or alkenyl radical containing 4 to about 22 carbon atoms, G is a sugar residue containing 5 or 6 carbon atoms and p 1 to about 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e., the distribution of mono- and oligoglycosides and stands for a number between 1 and about 10. While p must always be an integer in the individual molecule and can assume the values p=1 to 6, the value p for a certain alkyl oligoglycoside is an analytically determined arithmetical quantity, which usually represents a fractional number. Preferably alkyl and/or alkenyl oligoglycosides with an average degree of oligomerization p of about 1.1 to about 3.0 are used. From an application technology point of view, those alkyl and/or alkenyl oligoglycosides are preferred whose degree of oligomerization is less than about 1.7 and lies between about 1.2 and about 1.4. The alkyl or alkenyl radical $R^4$ can be derived from primary alcohols containing 4 to about 11, preferably 8 to about 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or during the hydrogenation of aldehydes from Roelen's oxo synthesis. Preferred are alkyl oligoglucosides with a chain length of $C_5-C_{10}$ (DP=1 to 3), which are obtained as a preliminary step in the distillative separation of technical $C_8-C_{18}$ coconut-fatty alcohol and may be contaminated with less than about 6% by weight of $C_{12}$ alcohol, and alkyl oligoglucosides based on technical $C_{9/11}$ oxoalcohols (DP=1 to 3). The alkyl or alkenyl radical $R^{15}$ can also be derived from primary alcohols having about 12 to about 22, preferably about 12 to about 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened $C_{12/14}$ coconut alcohol with a DP of 1 to 3.

Sugar surfactants of the fatty acid N-alkyl polyhydroxyalkylamide type, a nonionic surfactant of formula (Tnio-3)

$$R^5CO-NR^6-[Z] \quad \text{(Tnio-3)}$$

in which $R^5CO$ is an aliphatic acyl radical containing 6 to about 22 carbon atoms, R6 is hydrogen, an alkyl or hydroxyalkyl radical containing 1 to 4 carbon atoms and [Z] is a linear or branched polyhydroxyalkyl radical containing 3 to about 12 carbon atoms and 3 to about 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxyalkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

$$R^7CO-(NR^8)-CH_2-[CH(OH)]_4-CH_2OH \quad \text{(Tnio-4)}$$

Preferably, glucamides of the formula (Tnio-4) are used as fatty acid-N-alkyl polyhydroxyalkylamides, in which $R^8$ represents hydrogen or an alkyl group and $R^7CO$ represents the acyl radical of caproic acid, caprylic acid, capric acid, Lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid or erucic acid or their technical mixtures. Particularly preferred are fatty acid N-alkyl glucamides of the formula (Tnio-4), which are obtained by reductive amination of glucose with methylamine and subsequent acylation with lauric acid or C12/14 coconut fatty acid or a corresponding derivative. Furthermore, polyhydroxyalkylamides can also be derived from maltose and palatinose.

The sugar surfactants may preferably be present in the compositions used according to the present disclosure in amounts of about 0.1-about 20% by weight, based on the total composition. Amounts of about 0.5-about 15 wt. % are preferred and amounts of about 0.5-about 7.5 wt. % are particularly preferred.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with about 2 to about 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R contains 6 to about 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Particularly good results were obtained when an agent (b) containing at least one ethoxylated fatty alcohol with a degree of ethoxylation of about 80 to about 120 was used in the process according to the present disclosure.

In another very particularly preferred embodiment, an agent according to the present disclosure is exemplified in that it comprises at least one nonionic surfactant of the formula (T-I),

wherein Ra represents a saturated or unsaturated, straight or branched $C_8$-$C_{24}$ alkyl group, preferably a saturated, straight $C_{16}$-bis $C_{18}$ alkyl group, and n is an integer from about 80 to about 120, preferably an integer from about 90 to about 110, and particularly preferably the number 100.

A particularly well-suited nonionic surfactant of this type bears the trade name Brij® S 100 or Brij® S 100 PA SG. This is stearyl alcohol, ethoxylated with about 100 EO, which is commercially available from Croda® and has the CAS number 9005-00-9.

Furthermore, particularly good results were obtained when an agent according to the present disclosure was used which contained at least one ethoxylated fatty alcohol with a degree of ethoxylation of about 10 to about 40.

In another very particularly preferred embodiment, an agent according to the present disclosure is exemplified in that it comprises at least one nonionic surfactant of the formula (T-II),

wherein
Rb is a saturated or unsaturated, unbranched or branched $C_8$-$C_{24}$ alkyl group, preferably a saturated, unbranched $C_{16}$- to $C_{18}$ alkyl group, and m an integer from about 10 to about 40, preferably an integer from about 20 to about 35, and particularly preferably the number 30.

A particularly well-suited nonionic surfactant of this type is ceteareth-30. Ceteareth-30 is a mixture of cetyl alcohol and stearyl alcohol, each ethoxylated with about 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin® B3 from BASF®.

It has been found to be quite preferred if the composition contains both at least one nonionic surfactant of formula (T-I) and at least one nonionic surfactant of formula (T-II).

Medium Solvent

The use of solvents has continued to produce very good results. For this reason, the composition according to the present disclosure may additionally contain at least one solvent as an optional component.

Suitable solvents may include, for example, solvents selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol. The use of 1,2-propylene glycol is particularly preferred.

In another very particularly preferred embodiment, a composition according to the present disclosure is exemplified in that it comprises at least one solvent selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol, very preferably 1,2-propylene glycol.

1,2-Propylene glycol is alternatively referred to as 1,2-propanediol and bears the CAS numbers 57-55-6 [(RS)-1,2-dihydroxypropane], 4254-14-2 [(R)-1,2-dihydroxypropane] and 4254-153 [(S)-1,2-dihydroxypropane]. Ethylene glycol is alternatively known as 1,2-ethanediol and carries CAS number 107-21-1. Glycerol is alternatively known as 1,2,3-propanetriol and carries CAS number 56-81-5. Phenoxyethanol has the Cas number 122-99-6.

All the solvents described previously are commercially available from various chemical suppliers, such as Aldrich® or Fluka®.

By using the above-mentioned solvents in suitable application quantities, a particularly stable agent can be obtained, with which color results of very high intensity can be obtained on the keratinous material.

In a further preferred embodiment, an agent according to the present disclosure is exemplified in that it comprises—based on the total weight of the agent-one or more solvents in a total amount of about 1.0 to about 20.0% by weight, preferably about 2.0 to about 15.0% by weight, more preferably about 3.0 to about 15.0% by weight and very particularly preferably about 4.0 to about 10.0% by weight of 1,2-propylene glycol.

In another very particularly preferred embodiment, a composition according to the present disclosure is exemplified in that it contains—based on the total weight of the composition—about 1.0 to about 95.0% by weight, preferably about 2.0 to about 15.0% by weight, more preferably about 3.0 to about 15.0% by weight and very particularly preferably about 4.0 to about 10.0% by weight of 1,2-propylene glycol.

Other Optional Ingredients in the Agent

In addition to the ingredients already described, the agent may also contain additional optional ingredients.

For example, the agent may contain a film-forming polymer. The film-forming polymer may be selected, for example, from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, explicitly very particularly preferred polyvinylpyrrolidone (PVP).

Further suitable film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of oleofins, such as cycloolefins, butadiene, isoprene or styrene, vinyl ethers, vinyl amides, the esters or amides of (meth)acrylic acid having at least one $C_1$-$C_{20}$ alkyl group, an aryl group or a C2-C10 hydroxyalkyl group.

Other film-forming polymers may be selected from the homo- or copolymers of isooctyl (meth)acrylate; isononyl (meth)acrylate; 2-ethylhexyl (meth)acrylate; lauryl (meth)acrylate); isopentyl (meth)acrylate; n-butyl (meth)acrylate); isobutyl (meth)acrylate; ethyl (meth)acrylate; methyl (meth)acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth) acrylamides, in those with C2-C18 alkyl groups, such as N-ethyl-acrylamide, N-tert-butyl-acrylamide, le N-octyl-acrylamide; N-di(C1-C4)alkyl-(meth)acrylamide.

Other suitable anionic copolymers include copolymers of acrylic acid, methacrylic acid or their $C_1$-$C_6$ alkyl esters, as sold under the INCI declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Polymers on the market include Aculyn® 22 (Acrylate/Steareth-20 Methacrylate Copolymer), Aculyn® 28 (Acrylate/Beheneth-25 Methacrylate Copolymer), Structure 2001® (Acrylates/Steareth-20 Itaconate Copolymer), Structure 3001® (Acrylate/Ceteth-20 Itaconate Copolymer), Structure Plus® (acrylate/aminoacrylate $C_{10}$-30 alkyl PEG-20 itaconate copolymer), Carbopol® 1342, 1382, Ultrez 20, Ultrez 21 (acrylate/C10-30 alkyl acrylate crosspolymer), Synthalen W 2000® (acrylate/palmeth-25 acrylate copolymer) or Soltex® OPT (acrylate/C12-22 alkyl methacrylate copolymer) distributed by Rohme und Haas.

The homo- and copolymers of N-vinylpyrrolidone, vinyl-caprolactam, vinyl-(C1-C6)alkyl-pyrrole, vinyl-oxazole, vinyl-thiazole, vinylpyrimidine, vinylimidazole can be named as suitable polymers based on vinyl monomers.

Also suitable are the copolymers octylacrylamide/acrylates/butylaminoethyl methacrylate copolymer, such as those sold commercially under the trade names AMPHO-MER® or LOVOCRYL® 47 from NATIONAL STARCH, or the copolymers of acrylates/octylacrylamides sold under the trade names DERMACRYL® LT and DERMACRYL® 79 from NATIONAL STARCH.

Suitable olefin-based polymers include homopolymers and copolymers of ethylene, propylene, butene, isoprene and butadiene.

In another embodiment, the film-forming hydrophobic polymers may be the block copoylmers comprising at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF® under the trade name "Luvitol HSB".

If, in principle, both anionic and cationic and/or nonionic polymers can be used in the composition according to the present disclosure, it has proved particularly preferable not to use further ionic compounds or to use them only in small amounts. In other words, a particularly strong improvement in color intensity could be achieved when the agent was a predominantly non-ionic base and therefore contained cationic and anionic polymers either not at all or only in very small amounts. For this reason, it has been found to be particularly preferable if the total content of all anionic polymers contained in the agent is below about 0.10% by weight. Furthermore, it has been found to be particularly preferred if the total content of all cationic polymers contained in the agent is below about 0.1% by weight. The amount of catalytic or anionic polymer is related to the total weight of the agent.

In another very particularly preferred embodiment, an embodiment according to the present disclosure is exemplified in that—in relation to the total weight of the composition
  the total content of all anionic polymers contained in the composition is below about 0.10% by weight, and
  the total content of all cationic polymers contained in the composition is below about 0.10% by weight.

In addition to the non-ionic surfactants described above, the agents can in principle also contain one or more charged surfactants. The term surfactants refer to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —$COO^{(-)}$— or —$SO_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having about 8 to about 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —SO$_3$H group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to about 24 C atoms in the alkyl group. Typical examples of amphoteric or zwitterionic surfactants are alkylbetaines, alkylamidobetaines, amino-propionates, aminoglycinate, imidazoliniumbetaines and sulfobetaines.

Examples of ampholytic surfactants are N-cocosalkylaminopropionate, cocosacylaminoethylaminopropionate and $C_{12}$-$C_{18}$-acyl sarcosine.

In addition, the products may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Examples of cationic surfactants are

- quaternary ammonium compounds which, as hydrophobic radicals, may carry one or two alkyl chains with a chain length of about 8 to about 28 C atoms,
- quaternary phosphonium salts substituted with one or more alkyl chains with a chain length of about 8 to about 28 C atoms or
- tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of about 0.1 to about 45 wt. %, preferably about 1 to about 30 wt. % and most preferably about 1 to about 15 wt. %—based on the total weight of the respective agent.

Furthermore, an embodiment according to the present disclosure may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with about 12 to about 20 C atoms in the alkyl group and up to about 16 glycol ether groups in the molecule.

If, in principle, both anionic and cationic and/or non-ionic surfactants can be used in the composition according to the present disclosure, it has proved particularly preferable not to use further ionic compounds or to use them only in small quantities. In other words, a particularly strong improvement in color intensity could be achieved when the agent was a predominantly non-ionic base and therefore contained cationic and anionic surfactants either not at all or only in very small amounts. For this reason, it has been found to be particularly preferable if the total content of all anionic surfactants contained in the formulation is below about 0.1% by weight. Furthermore, it has been found to be particularly preferable if the total content of all cationic surfactants contained in the agent is below about 0.1% by weight. The amount of catalytic or anionic surfactant is related to the total weight of the product.

In another very particularly preferred embodiment, an embodiment according to the present disclosure is exemplified in that—in relation to the total weight of the composition

- the total content of all anionic surfactants contained in the composition is below about 0.1% by weight, and
- the total content of all cationic surfactants contained in the composition is below about 0.1% by weight.

The compositions may also contain other active ingredients, auxiliaries and additives, such as solvents, structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc Omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; Ceramides or pseudoceramides; vitamins, provitamins and vitamin precursors; plant extracts; fats and waxes such as fatty alcohols, beeswax, montan wax and kerosene's; Swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations according to the present disclosure in quantities of about 0.0001 to about 25 wt. % each, preferably about 0.0005 to about 15 wt. %, based on the total weight of the respective agent.

Agent pH Value

The pH value of the agent according to the present disclosure is preferably adjusted to a neutral to alkaline pH value. Most preferably, the agent has an alkaline pH value in the range of about 7.0 to about 11.5 preferably from about 8.0 to about 11.0, and most preferably from about 8.5 to about 10.5. Under basic conditions, the amino-functionalized silicone polymer (a1) can be dissolved or dispersed particularly well and without protonation.

Within the scope of a further preferred embodiment, an agent according to the present disclosure is exemplified in that it has a pH of from about 7.0 to about 11.5 preferably from about 8.0 to about 11.0, and particularly preferably from about 8.5 to about 10.5.

To adjust the desired pH, the agent (a) and/or (b) may contain at least one alkalizing agent. The pH values for the purposes of the present disclosure are pH values measured at a temperature of 22° C.

As alkalizing agents, the agents may contain, for example, ammonia, alkanolamines and/or basic amino acids.

The alkanolamines which can be used in the composition of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred according to the present disclosure are selected from 2-aminoethan-1-ol and/or 2-amino-2-methylpropan-1-ol. A particularly preferred embodiment is therefore exemplified in that the agent according to the present disclosure contains an alkanolamine selected from 2-aminoethan-1-ol and/or 2-amino-2-methylpropan-1-ol as alkalizing agent.

For the purposes of the present disclosure, an amino acid is an organic compound containing at least one protonatable amino group and at least one —COOH or —$SO_3H$ group in its structure. Preferred amino acids are amino carboxylic acids, in particular -(alpha)-amino carboxylic acids and ω-amino carboxylic acids, with -amino carboxylic acids being particularly preferred.

According to the present disclosure, basic amino acids are those amino acids which have an isoelectric point pI of greater than about 7.0.

Basic α-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent according to the present disclosure is therefore exemplified in that the alkalizing agent is a basic amino acid from the group arginine, lysine, ornithine and/or histidine.

In addition, the product may contain other alkalizing agents, especially inorganic alkalizing agents. Inorganic alkalizing agents usable according to the present disclosure are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, a process according to the present disclosure is exemplified in that the colorant (a) comprises at least one alkalizing agent selected from the group of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Process for Dyeing Keratin Material

The agents described above can be excellently used in processes for dyeing keratinous material, especially human hair.

A second object of the present disclosure is therefore a method for coloring keratinous material, in particular human hair, comprising the following steps:

(1) Application of a coloring agent to the keratinous material, wherein the coloring agent is an agent as disclosed in detail in the description of the first subject matter of the present disclosure, (2) Exposure of the colorant to the keratinous material and (3) Rinse out the dye with water.

In step (1) of the process according to the present disclosure, the agent of the first portion of the present disclosure is applied to the keratinous material, which is most preferably human hair.

In step (2) of the process according to the present disclosure, the agent is then allowed to act on the keratinous material after its application. In this context, different exposure times of, for example, about 30 seconds to about 60 minutes are conceivable.

However, a major advantage of the dyeing system according to the present disclosure is that an intensive color result can be achieved even in very short periods after short exposure times. For this reason, it is advantageous if the application mixture remains on the keratin material only for comparatively short periods of time after its application, from about 30 seconds to about 15 minutes, preferably from about 30 seconds to about 10 minutes, and particularly preferably from about 1 to about 5 minutes.

In a further preferred embodiment, a method according to the present disclosure is exemplified by:

(2) Exposure of the colorant to the keratinous material for a period ranging from about 30 seconds to about 15 minutes, preferably from about 30 seconds to about 10 minutes, and most preferably from about 1 to about 5 minutes.

Finally, following the action of the application mixture on the keratin material, it is rinsed with water in step (3) of the process.

Here, in one embodiment, the application mixture can be washed out with water only, i.e., without the aid of an after-treatment agent or a shampoo. The use of a post-treatment agent or conditioner in step (6) is also conceivable in principle.

However, to solve the task according to the present disclosure and to increase the convenience of use, it has proved particularly preferable to rinse the agent in step (3) exclusively with water without the aid of a further after-treatment agent, shampoo or conditioner.

In a further preferred embodiment, a method according to the present disclosure is exemplified by:

(3) Rinse out the dye with water only.

Concerning the further preferred embodiments of the method according to the present disclosure, mutatis mutantis what has been said about the composition according to the present disclosure applies.

Examples

1. Formulations
The following formulations were prepared (all data in wt. % unless otherwise stated):

| Colorants | (V1) | (V2) | (E1) | (E2) | (E3) | (E4) |
|---|---|---|---|---|---|---|
| Cetyl alcohol | 6.0 | 6.0 | 6.0 | 6.0 | 6.0 | 6.0 |
| Lauryl alcohol | 6.0 | 6.0 | 6.0 | 6.0 | 6.0 | 6.0 |
| Ceteareth-30 (Cetearyl alcohol, ethoxylated 30 EO) | 3.0 | 3.0 | 3.0 | 3.0 | 3.0 | 3.0 |
| 1.2-propanediol | 6.0 | 6.0 | 6.0 | 6.0 | 6.0 | 6.0 |
| Lavanya Belmont (organic pigment, Neelikon Blue, 29H,31H-Phthalocyanine, copper complex, CI 74160) (a2) | 0.10 | 0.30 | 0.10 | 0.10 | 0.10 | 0.10 |
| Lavanya Revolutum Neelikon Yellow (organic pigment, Yellow # 401, CI 11680) (a2) | 0.60 | 1.80 | 0.60 | 0.60 | 0.60 | 0.60 |
| Lavanya Zuni (organic pigment, Neelikon Red, 111P0200, CI 12490) (a2) | 0.30 | 0.90 | 0.30 | 0.30 | 0.30 | 0.30 |
| Amino silicone (Dow® Coming 2-8566 (Siloxanes and Silicones, 3-[(2-aminoethyl)amino]-2-methylpropyl Me, Di-Me-Siloxanes) (a1) | 0.5 | 0.5 | 1.1 | 1.5 | 2.0 | 2.5 |
| Ammonia (25% aqueous solution) | 0.2 | 0.2 | 0.2 | 0.2 | 0.2 | 0.2 |
| Water | ad 100 | ad 100 | ad 100 | ad 100 | ad 100 | ad 100 |
| Total quantity (a1) | 0.5 | 0.5 | 1.1 | 1.5 | 2.0 | 2.5 |
| Total quantity (a2) | 1.0 | 3.0 | 1.0 | 1.0 | 1.0 | 1.0 |
| Weight ratio (a2)/(a1) | 2.0 | 6.0 | 0.9 | 0.67 | 0.5 | 0.4 |

V = Comparison
E = according to present disclosure

2. Application

The coloring was done on hair strands from Kerling, type "Euronatural hair white" (ENH). Prior to dyeing, the hair strands were colorimetrically measured using a Datacolor Spectra flash 450 colorimeter.

Then the respective agent was applied to the hair strands (liquor ratio: 1 g agent per g strand of hair) and left to act for three minutes. Subsequently, the hair strand was thoroughly washed (1 minute) with water, dried and then measured again colorimetrically.

The dE value used for evaluating the color intensities is derived from the measured L*a*b* colorimetric values as follows:

$$dE=[(L_t-L_0)^2+(a_t-a_0)^2+(b_t-b_0)^2]^{1/2}$$

L0, a0 and b0 = measured values before staining $L_t$, $a_t$ and $b_t$ = measured values after staining The greater the dE value, the greater the color distance to the uncolored hair and the higher the color intensity.

| Colorants | ENH uncolored | (V1) | (V2) | (E1) | (E2) | (E3) | (E4) |
|---|---|---|---|---|---|---|---|
| L-value | 72.02 | 43.13 | 52.13 | 34.18 | 33.58 | 31.43 | 29.80 |
| a-value | 3.32 | 4.78 | 2.65 | 6.26 | 6.31 | 6.72 | 6.65 |
| b-value | 26.15 | 14.31 | 16.22 | 12.31 | 12.76 | 12.73 | 12.85 |
| dE | — | 31.3 | 22.2 | 40.4 | 40.8 | 42.9 | 44.4 |
| Weight ratio (a2)/(a1) | | 2.0 | 6.0 | 0.9 | 0.67 | 0.5 | 0.4 |

The colorations obtained with the formulations according to the present disclosure were darker or more intense (lower L value) and possessed a greater color distance compared to the undyed hair (greater dE value).

The invention claimed is:

1. An agent for dyeing keratinous material, comprising
   (a1) at least one amino-functionalized silicone polymer, and
   (a2) at least one pigment, wherein
   a weight ratio of all the at least one pigments (a2) in the agent to all the at least one amino-functionalized silicone polymers (a1) in the agent is not more than about 0.95, and wherein the agent comprises water and the agent has a pH of from about 7.0 to about 11.5.

2. The agent according to claim 1, wherein the agent comprises the at least one amino-functionalized silicone polymer (a1) having at least one secondary amino group.

3. The agent according to claim 1, wherein the agent comprises the at least one amino-functionalized silicone polymer (a1) comprising at least one structural unit of the formula (Si amino),

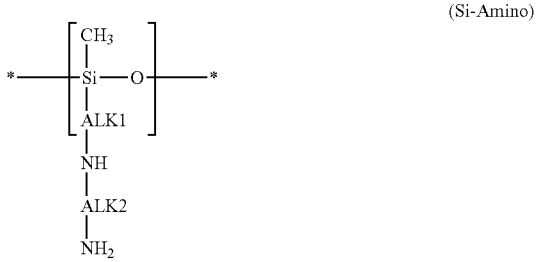

(Si-Amino)

where
ALK1 and ALK2 independently represent a linear or branched $C_1$-$C_{20}$ divalent alkylene group.

4. The agent according to claim 1, wherein the agent comprises the at least one amino-functionalized silicone polymer (a1) comprising structural units of the formula (Si-I) and of the formula (Si-II)

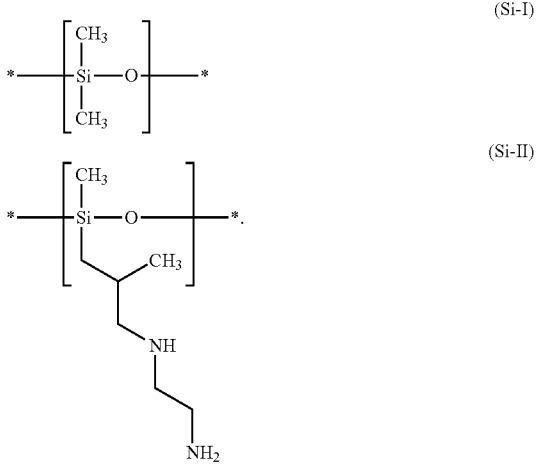

5. The agent according to claim 1, wherein the agent comprises—based on a total weight of the agent—the one or more amino-functionalized silicone polymers (a1) in a total amount of from about 0.1 to about 8.0% by weight.

6. The agent according to claim 1, wherein the at least one pigment (a2) is selected from the group of colored metal oxides; metal hydroxides; metal oxide hydrates; silicates; metal sulfides; complex metal cyanides; metal sulfates; bronze pigments; mica- or mica-based colored pigments coated with a metal oxide, a metal oxychloride, or a combination of the metal oxide and the metal oxychloride; and combinations thereof.

7. The agent according to claim 1, wherein the at least one pigment (a2) is selected from the group of carmine, quinacridone, phthalocyanine, Sorgho, blue pigments with the color index numbers CI 42090, CI 69800, CI 69825, CI 73000, CI 74100, and/or CI 74160, yellow pigments with the color index numbers CI 11680, CI 11710, CI 15985, CI 19140, CI 20040, CI 21100, CI 21108, CI 47000, and/or CI 47005, green pigments with Color Index numbers CI 61565, CI 61570, and/or CI 74260, orange pigments with Color Index numbers CI 11725, CI 15510, CI 45370, and/or CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470, and combinations thereof.

8. The agent according to claim 1, wherein the agent comprises—based on a total weight of the composition—the one or more pigments (a2) in a total amount of from about 0.01 to about 10.0% by weight.

9. The agent according to claim 1, wherein the weight ratio of all the at least one pigments (a2) in the agent to all at least one amino-functionalized silicone polymers (a1) in the agent is from about 0.10 to about 0.80.

10. The agent according to claim 1, wherein the agent further comprises one or more fat constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

11. The agent according to claim 1, wherein the agent further comprises at least one nonionic surfactant of the formula (T-I),

(T-I)

wherein
Ra is a saturated or unsaturated, unbranched or branched $C_8$-$C_{24}$ alkyl group, and
n is an integer from about 80 to about 120.

12. The agent according to claim 1, wherein the agent further comprises at least one nonionic surfactant of the formula (T-II),

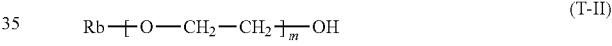

(T-II)

wherein
Rb represents a saturated or unsaturated, unbranched or branched $C_8$-$C_{24}$ alkyl group, and
m an integer from about 10 to about 40.

13. The agent according to claim 1, wherein the agent further comprises at least one solvent selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol, benzyl alcohol, and combinations thereof.

14. The agent according to claim 1, wherein the agent further comprises an anionic surfactant in an amount of from zero to about 0.1% by weight, based on a total weight of the agent, and the agent further comprises a cationic surfactant in an amount of from zero to about 0.1% by weight, based on the total weight of the agent.

15. The agent according to claim 1, wherein the agent further comprises an anionic polymer in an amount of from zero to about 0.1% by weight, based on a total weight of the agent, and the agent further comprises a cationic polymer in an amount of from zero to about 0.1% by weight, based on the total weight of the agent.

16. A method for dyeing keratinous material, comprising the following steps:
(1) applying an agent to the keratinous material, wherein the agent comprises (a1) an amino-functionalized silicone polymer, and (a2) a pigment, wherein a weight ratio of all the pigments (a2) in the agent to all the amino-functionalized silicone polymers (a1) in the agent is not more than about 0.95;

(2) exposing the keratinous material to the agent; and
(3) rinsing the agent out of the keratinous material with water, and wherein the agent comprises water and the agent has a pH of from about 7.0 to about 11.5.

17. The method according to claim 16, wherein the (2) exposing the keratinous material to the agent comprises exposing the keratinous material to the agent for a period of from about 30 seconds to about 15 minutes.

18. The agent according to claim 1, wherein the weight ratio of all the at least one pigments (a2) in the agent to all at least one amino-functionalized silicone polymers (a1) in the agent is from about 0.35 to about 0.45.

19. The agent according to claim 1, wherein the weight ratio of all the at least one pigments (a2) in the agent to all at least one amino-functionalized silicone polymers (a1) in the agent is from about 0.35 to about 0.55.

* * * * *